United States Patent [19]  
Umezawa et al.

[11] 4,120,955  
[45] Oct. 17, 1978

[54] METHOD FOR PRODUCTION OF KANAMYCIN C AND ITS DERIVATIVES

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 799,806

[22] Filed: May 23, 1977

[30] Foreign Application Priority Data

Jun. 16, 1976 [JP] Japan ................................ 51-69759

[51] Int. Cl.$^2$ ........................ A61K 31/71; C07H 15/22
[52] U.S. Cl. ........................................ 424/180; 536/10; 536/17
[58] Field of Search ...................... 536/10, 17; 424/180

[56] References Cited

U.S. PATENT DOCUMENTS 3,929,762  12/1975  Umezawa et al. ...................... 536/10

OTHER PUBLICATIONS

Tipson et al., "Advances in Carbohydrate Chem. and Biochemistry," vol. 30, 1974, Academic Press, N. Y. pp. 183–189.

Primary Examiner—Johnnie R. Brown  
Attorney, Agent, or Firm—Herbert W. Taylor, Jr.

[57] ABSTRACT

Kanamycin C, 3'-deoxykanamycin C and 3'4'-dideoxykanamycin C are obtained by a new process comprising treating the primary 6'-amino group of a tetra-N-protected derivative of kanamycin B, 3'-deoxykanamycin B and 3', 4'-dideoxykanamycin B with a nitrite to convert said amino group into hydroxyl group and then removing the protective groups. 3'-Deoxykanamycin C and 3', 4'-dideoxykanamycin C are new semi-synthetic aminoglycosidic antibiotics.

6 Claims, No Drawings

METHOD FOR PRODUCTION OF KANAMYCIN C AND ITS DERIVATIVES

BACKGROUND OF THE INVENTION

1. Field of the Invention

This invention relates to production of kanamycin C and its deoxy derivatives from kanamycin B or deoxy derivatives of the latter. This invention further relates to deoxy-kanamycin C derivatives which are new compounds useful as semi-synthetic aminoglycosidic antibiotics.

More particularly, this invention relates to a process for the production of kanamycin C, 3'-deoxykanamycin C and 3',4'-dideoxykanamycin C which are represented by the following general formula (I):

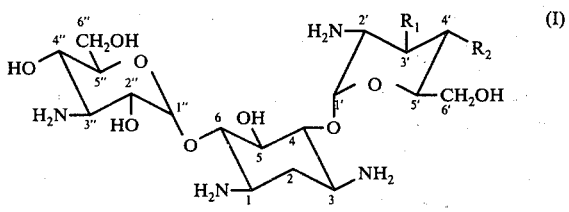

where $R_1$ and $R_2$ are both hydroxyl, or $R_1$ is hydrogen and $R_2$ is hydroxyl, or $R_1$ and $R_2$ are both hydrogen. This invention also relates to the new deoxy-kanamycin C derivatives, that is, 3'-deoxykanamycin C which is the compound of the formula (I) where $R_1$ is a hydrogen atom and $R_2$ is hydroxyl group, and 3',4'-dideoxykanamycin C which is the compound of the formula (I) where $R_1$ and $R_2$ are both a hydrogen atom.

2. Description of the Prior Art

We, the present inventors, have made research on new semi-synthetic derivatives of aminoglycosidic antibiotics on the basis of the previous findings which were obtained by H. Umezawa et al. with respect to the mechanism of resistance of bacteria to aminoglycosidic antibiotics owing to various inactivating enzymes produced by the resistant bacteria. For instance, 3',4'-dideoxykanamycin B and 3'-deoxykanamycin B were synthetized as the deoxy derivatives of kanamycin B which are active against the resistant bacteria producing aminoglycoside 3'-phosphotransferases (see U.S. Pat. Nos. 3,753,973 and 3,929,762; H. Umezawa's "Advances in Carbohydrate Chemistry and Biochemistry" Vol. 30, page 183 (1974); and "Drug Action and Drug Resistance in Bacteria" Vol. 2, page 211 (1975)). 3',4'-Dideoxykanamycin B has been used widely in therapeutic treatment of infections caused by a variety of the resistant bacteria, including *Pseudomonas aeruginosa*. However, it has been found that these deoxy derivatives of kanamycin B can be inactivated by aminoglycoside 6'-acetyltransferases capable of acetylating the 6'-amino group of the deoxykanamycin B molecule and hence are not able to inhibit the growth of such resistant bacteria producing 6'-acetyltransferases.

SUMMARY OF THE INVENTION

In these circumstances, we have made further research, and as a result we have succeeded in synthetizing kanamycin C and deoxy derivatives of kanamycin C which inherently cannot be inactivated by 6'-acetyltransferases. The synthesis of kanamycin C and its deoxy derivatives is performed by substituting a hydroxyl group for the 6'-amino group of kanamycin B or its deoxy derivatives. It has also been found that the new deoxy derivatives of kanamycin C according to the present invention do not exhibit an improved antibacterial activity to the sensitive bacteria but have advantageously a remarkably lowered acute toxicity, as compared to the above-mentioned deoxy derivatives of kanamycin B. Moreover, we have succeeded in developing a process by which kanamycin C as well as the deoxy derivatives of kanamycin C can be synthetized with advantages.

Hithertofore, the production of kanamycin C is performed in a poor efficiency for the reason that kanamycin C can be recovered only as a minor by-product from a fermentation broth of *Streptomyces kanamyceticus* used for the production of kanamycin A and kanamycin B (see the "Journal of Antibiotics" A. Vol. 14, page 156 (1961)).

An object of the present invention is to provide such new deoxy derivatives of kanamycin C which inherently cannot be inactivated by 6'-acetyltransferases and exhibits a low toxicity. Other object of the present invention is to provide a new process for the synthesis of kanamycin C and its deoxy derivatives which can be operated in a facile way and with a high efficiency. Another objects will be clear from the following descriptions.

DETAILED DESCRIPTION OF THE INVENTION

According to a first aspect of this invention, therefore, there is provided a process for the production of kanamycin C, 3'-deoxykanamycin C or 3',4'-dideoxykanamycin C, that is, a kanamycin C compound of the general formula (I):

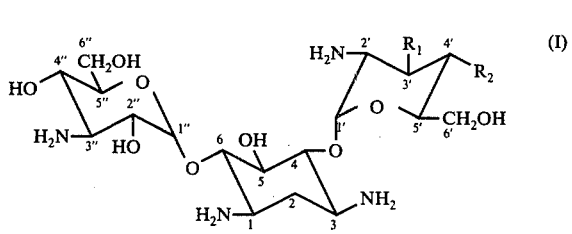

wherein $R_1$ and $R_2$ each is hydroxyl, or $R_1$ is hydrogen and $R_2$ is hydroxyl, or $R_1$ and $R_2$ each is hydrogen, which comprises the steps of:

protecting with an amino-protecting group selectively the primary 6'-amino group of a kanamycin B compound represented by the general formula (II):

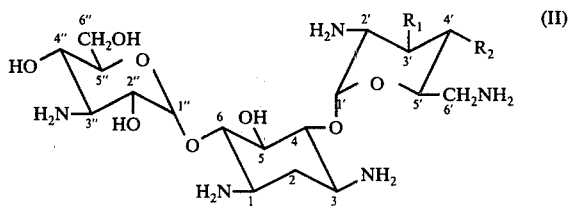

wherein $R_1$ and $R_2$ have the same meanings as defined above, to produce the 6'-N-protected derivative of said kanamycin B compound, protecting with another amino-protecting group the remaining four, secondary amino groups of the 6'-N-protected derivative of the kanamycin B compound, to produce the penta-N-protected derivative of said kanamycin B compound, removing selectively the amino-protecting group from the primary 6'-amino group of the penta-N-protected derivative, to prepare the 1,3,2',3''-tetra-N-protected derivative of said kanamycin B compound, treating the primary 6'-amino group so liberated of the 1,3,2',3'-tetra-N-protected derivative with a nitrite to convert the 6'-amino group into a hydroxyl group and thereby to produce the corresponding 6'-hydroxyl derivative, and removing the amino-protecting group from the four, secondary amino groups of the 6'-hydroxyl derivative, to produce the compound of the formula (I).

The present process may include a further step of reacting the compound of the formula (I) so obtained, with a pharmaceutically acceptable acid to produce a corresponding acid-addition salt of said compound of the formula (I), if desired.

The process of the present invention is carried out in the manner as described below. Firstly, as the starting compound is employed either kanamycin B, namely the compound of the formula (II) where $R_1$ and $R_2$ each is hydroxyl, or 3'-deoxykanamycin B, namely the compound of the formula (II) where $R_1$ is hydrogen and $R_2$ is hydroxyl, or 3',4'-dideoxykanamycin B, namely the compound of the formula (II) where $R_1$ and $R_2$ each is hydrogen. This starting kanamycin B compound is protected selectively at its primary 6'-amino group with a known amino-protecting group to prepare the 6'-N-protected derivative of the formula (III):

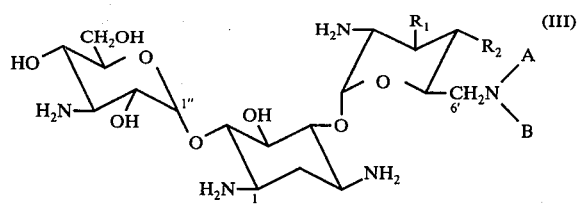

wherein $R_1$ and $R_2$ have the same meanings as defined above, A is a hydrogen atom and B is a known monovalent amino-protecting group, or A taken together with B forms a known di-valent amino-protecting group.

As describd in the specification of U.S. Pat. Nos. 3,753,973 and 3,929,762, there is known a method of preparing a 6'-N-protected derivative of kanamycin B or 3',4'-dideoxykanamycin B in a high yield by reacting kanamycin B or 3',4'-dideoxykanamycin B with an appropriate reagent for introduction of an amino-protecting group which is conventionally employed in the known synthesis of peptides, so that the primary 6'-amino group of the highest reactivity among the five amino groups of the kanamycin B compound is selectively protected by said amino-protecting group. It is also possible to protect selectively the primary 6'-amino group of 3'-deoxykanamycin B in the same manner as in the preparation of the 6'-N-protected derivatives of kanamycin B and 3',4'-dideoxykanamycin B, so that the 6'-N-protected derivative of 3'-deoxykanamycin B is afforded. Thus, in the process of the present invention, the preparation of the 6'-N-protected derivative (III) may be performed in the same manner as in the aforesaid known method using the appropriate reagent for introduction of an amino-protecting group. For the protective group of selectively blocking the primary 6'-amino group is used such an amino-protecting group which is conventional, though it is preferred to employ such one which is removable readily. Suitable examples of the monovalent amino-protecting group which are available for blocking the primary 6'-amino group in the process of the present invention include an alkoxycarbonyl group such as tert-butoxycarbonyl (hereinafter abbreviated as BOC) and tert-amyloxycarbonyl; a cycloalkyloxycarbonyl group such as cyclohexyloxycarbonyl, an aralkyloxycarbonyl group such as benzyloxycarbonyl (hereinafter abbreviated as Z) and p-methoxybenzyloxycarbonyl; and an acyl group, for example, a substituted alkanoyl group such as trifluoroacetyl and o-nitrophenoxyacetyl. Preferable examples of the di-valent amino-protecting group include the one of Schiff base type such as salicylidene group. The amino-protecting group may be introduced into the primary 6'-amino group of the kanamycin B compound (II) in the same manner as described e.g. in the specification of U.S. Pat. Nos. 3,929,762 and 3,939,143 using the amino-protective group-introducing reagent in the form of an acid halide, acid azide, active ester or acid anhydride. It is preferred that the amino-protective group-introducing reagent is used in a 0.5 to 1.5 molar proportion per 1 molar proportion of the kanamycin B compound, as the desired 6'-N-protected derivative (III) is then obtained in a best yield and unreacted starting compound can be recovered in a good efficiency. The 6'-N-protected derivative (III) so obtained may be purified in a facile way by column-chromatography with a weakly acidic cation-exchange resin containing carboxyl functions.

In the second step, the 6'-N-protected derivative (III) so obtained is treated to protect the remaining four, secondary amino groups of the compound (III) with such an amino-protecting group which is of the nature different from the one already employed for blocking the primary 6'-amino group and which is cleavable but is unlikely to be cleaved to such an extent that it cannot be cleaved under the reaction conditions required for the subsequent step of removing selectively the amino-protecting group from the blocked primary 6'-amino group. If required, one or more of the hydroxyl groups of the compound (III) may be protected by a known hydroxyl-protecting group such as acetyl. In this way, there is prepared the penta-N-protected derivative of the formula (IV):

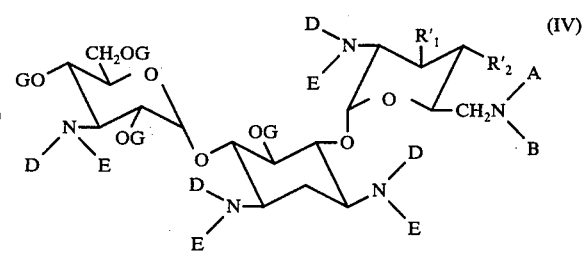

wherein $R'_1$ and $R'_2$ each is a hydrogen atom or a hydroxyl group or a protected hydroxyl group; A and B have the same meanings as defined above; D is a hydrogen atom and E is an amino-protecting group of a different nature from the amino-protecting group represented by B, or D together E forms a di-valent amino-protecting group of a different nature from the di-valent amino-protecting group represented by both A and B, all of the groups G are each a hydrogen atom, or at least one of the groups G is a hydroxyl-protecting group and the remaining groups G is or are each a hydrogen atom. For the amino-protecting group used to block the four, secondary amino groups of the 6'-N-protected derivative (III), there may be selected from amongst the above-mentioned various kinds of the amino-protecting group such one of the different nature from that which has been employed to block the 6'-amino group. However, it is necessary that the amino-protecting groups selected to block the four, secondary amino groups should be substantially non-cleavable under the reaction conditions of the subsequent step where the amino-protecting group bonded to the primary 6'-amino group is removed therefrom. The amino-protecting groups may be introduced into the secondary amino groups in the same manner as described for the protection of the primary 6'-amino group, provided that the reagent for introduction of the amino-protecting group is charged in a 4 molar or more proportion per 1 molar proportion of the 6'-N-protected derivative (III). In addition to the various kinds of the amino-protecting groups listed hereinbefore, acetyl group which has a relatively low tendency to be cleaved is available and is preferred for blocking the four, secondary amino groups of the compound (III). Blocking of the secondary amino groups of the 6'-N-protected derivative (III) with acetyl group may be performed in such a manner that a solution of the compound (III) in anhydrous methanol is reacted with an excess of acetic anhydride at ambient temperature for a short reaction time, preferably for 5 hours. If necessary, it is also possible that the secondary amino groups and one or more hydroxyl groups of the 6'-N-protected derivative (III) are protected concurrently with a protective group of the same nature. For instance, the 6'-N-protected derivative (III) may be reacted with a mixture of acetic anhydride and sodium acetate or with anhydrous sodium acetate in pyridine to give the N,O-acetylated derivative (IV) which is formed by acetylation of the four, secondary amino groups and one or more hydroxyl groups of the 6'-N-protected derivative (III). In the process of the present invention, however, nothing is normally requred in this stage more than that the four, secondary amino groups of the compound (III) are blocked.

In the third step, the penta-N-protected derivative (IV) is so processed that the amino-protecting group is removed selectively from the primary 6'-amino group of the compound (IV), to afford the 1,3,2',3''-tetra-N-protected derivative of the following general formula (V):

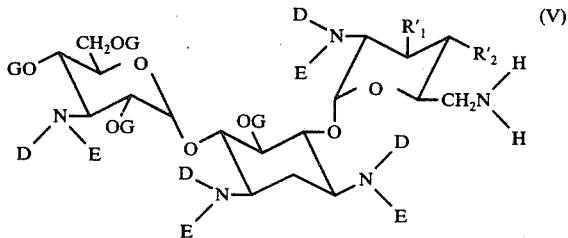

wherein $R'_1$, $R'_2$, D, E and G have the same meanings as defined before. The reaction for selective removal of the amino-protecting group from the primary 6'-amino group of the penta-N-protected derivative (IV) may be conducted in a known manner. Thus, when the amino-protecting group for the primary 6'-amino group is an aralkyloxycarbonyl group such as benzyloxycarbonyl or is o-nitrophenoxyacetyl group, it may be removed by subjecting to catalytic reduction with hydrogen in solution in water, methanol, acetic acid or a mixed solvent of two or more of these substances in the presence of a catalyst such as palladium or platinum. When the amino-protecting group is of the other natures, it may be removed by subjecting to hydrolysis in a weakly acidic solution. For instance, the BOC group may readily be removed by treating with a solution of 90% trifluoroacetic acid in water at ambient temperature for 1 hour or less. In this way, the 6'-amino derivative (V) as desired may be afforded. In carrying out the process of the present invention, it is most preferred that benzyloxycarbonyl group or BOC group is selected for the protection of the primary 6'-amino group, while acetyl group is selected for the protection of the four, secondary amino groups.

In a further step, the 6'-amino compound (V) obtained as above is then treated with a nitrite so that the 6'-amino group is converted into a hydroxyl group (this conversion may be called deamination) to give the 6'-hydroxyl product of the general formula (VI):

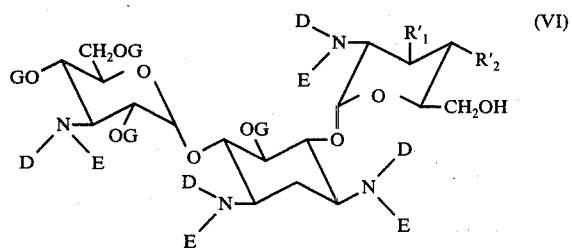

wherein $R'_1$, $R'_2$, D, E and G have the same meanings as defined hereinbefore. For conducting this deamination step of the 6'-amino group, an alkali metal nitrite may be suitable as the nitrite. Sodium nitrite is most preferred. The deamination of the 6'-amino compound (V) with a nitrite in this step may be carried out in a facile way by admixing a solution of the 6'-amino compound (V) in aqueous acetic acid with sodium nitrite under ice-cooling (at 0°-10° C.) and stirring, and then allowing the admixture to raise to ambient temperature and effecting the reaction at ambient temperature for 2 hours or more. In this way, the 6'-hydroxyl product (VI) is produced.

In the final step, the 6'-hydroxyl product (VI) so obtained is subjected to the treatment for removal of the amino-protecting group from the four, secondary amino groups of the 6'-hydroxyl product and occasionally also to the treatment for removal of the hydroxyl-protecting group, if present. The removal of the amino-protecting group from the secondary amino groups may be performed in a known manner. When the protective group is acetyl, this may be removed by alkaline hydrolysis, preferably in a manner that the compound (VI) is heated in 2N aqueous sodium hydroxide solution for 7 hours or more under reflux.

Concurrently or subsequently to the removal of the amino-protecting group from the secondary amino groups of the compound (VI), the removal of the hydroxyl-protecting group is conducted, if necessary, that is, if the hydroxyl-protecting group is present or remaining. The removal of the remaining whole protective groups from the 6'-hydroxyl compound (VI) gives the final compound of the formula (I) in a favorable yield. For instance, in case one or more hydroxyl groups of the 6'-hydroxyl compound (VI) has been protected by an ester-forming group such as acetyl, the hydroxyl-protecting group of this type such as O-acetyl group may be removed at the same time when the removal of the amino-protecting group is effected by alkaline hydrolysis as stated above.

The deoxy-kanamycin C derivatives of the formula (I) (including kanamycin C itself) obtained by the above consecutive steps of the process of the present invention may be isolated and purified efficiently by subjecting to column-chromatography on silica gel or column-chromatography on a cation-exchanger. It is recommendable that the purification is carried out chromatographically using a weakly acidic cation-exchanger resin containing carboxylic functions, such as Amberlite CG-50 ($NH_4^+$-form or a mixture of $NH_4^+$-form and $H^+$-form) developed with diluted aqueous ammonia as the eluent. Furthermore, although the product coming from each of the successive steps of the present process may be purified by chromatography on silica gel before it is charged into each subsequent step, the product may be recovered in the form of a crude product by concentrating the reaction solution of each step to dryness under reduced pressure and the crude product may directly be used in each subsequent step without being purified.

Amongst the compounds of the formula (I) produced by the process according to the first aspect of the present invention, 3'-deoxykanamycin C and 3',4'-dideoxykanamycin C are new compounds which are useful as semi-synthetic aminoglycosidic antibiotic. According to a second aspect of the present invention, therefore, there is provided a deoxykanamycin C compound of the formula (I'):

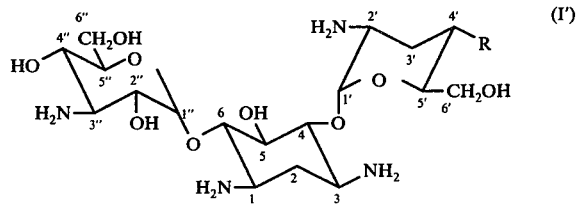

wherein R is a hydroxyl group or hydrogen atom, and an acid-addition salt thereof.

The new compounds 3'-deoxykanamycin C and 3',4'-dideoxykanamycin C according to the present invention have the following chemical, physical and biological properties:

3'-Deoxykanamycin C is a substance in the form of a colorless crystalline powder which does not show any definite melting point but decomposes at a temperature of 180°-220° C. It shows a specific optical rotation $[\alpha]_D^{26} = +110°$ (c 1, water). Its elemental analysis is coincident with the theoretical values of $C_{18}H_{36}N_4O_{10}\cdot\frac{1}{2}$ $H_2O$ (C 43.81%, H 7.56%, N 11.35%). This substance gives a single spot positive to ninhydrin reaction at Rf 0.22 by thin layer chromatography on silica gel (available under a trade name "ART 5721," a product of Merck Company, Germany) developed with butanol-ethenol-chloroform-17% aqueous ammonia (4:5:2:5 by volume) and at Rf 0.39 by the same thin layer chloromatography developed with chloroform-methanol-17% aqueous ammonia (1:4:2 by volume) as the developement solvent, respectively.

3',4'-Dideoxykanamycin C is a substance in the form of a colorless crystalline powder which does not show any definite melting point but decomposes over 200°-220° C. It shows a specific optical rotation $[\alpha]_D^{26} = +118°$ (c, 1, water). Its elemental analysis is coincident with the theoretical values of $C_{18}H_{36}N_4O_9\cdot\frac{1}{2}$ $H_2O$ (C 46.84%, H 8.08%, N 12.14%). In mass spectrometry, it gives a value of m/e 452 ($M^+$). This substance gives a single spot positive to ninhydrin at Rf 0.33 by the above-mentioned thin layer chromatography on silica gel using the first-mentioned developement solvent and at Rf 0.48 by the same thin layer chromatography on silica gel using the second-mentioned developement solvent.

The minimum inhibitory concentrations (mcg/ml) of kanamycin C, 3'-deoxykanamycin C and 3',4'-dideoxykanamycin C against various microorganisms were determened according to serial dilution method using nutrient agar medium at 37° C., the estimation being effected after 18 hours incubation. For comparison, the minimum inhibitory concentrations of 3',4'-dideoxykanamycin B (abbreviated as DKB) 3'-deoxykanamycin B (abbreviated as DKMB) were also determined in the same manner as described above.

The antibacterial spectra of these substances are shown in Table 1 below.

Table 1

| Test Organisms | Minimum Inhibitory Concentrations (mcg/ml) | | | | |
|---|---|---|---|---|---|
| | Kanamycin C | 3'-Deoxy-kanamycin C | 3',4'-Dideoxy-kanamycin C | DKB | DKMB |
| *Staphylococcus aureus* FDA 209P | 1.56 | 3.13 | 6.25 | <0.20 | <0.20 |
| *Mycobacterium smegmatis* ATCC 607 | 12.5 | 25 | 50 | 0.39 | 0.39 |
| *Escherichia coli* NIHJ | 3.13 | 12.5 | 12.5 | 0.39 | 0.78 |
| *Escherichia coli* K-12 | 3.13 | 12.5 | 25 | 0.78 | 0.39 |
| *Escherichia coli* K-12 R5 | 3.13 | 12.5 | 12.5 | — | — |
| *Escherichia coli* K-12 ML 1629 | >100 | 12.5 | 12.5 | 0.78 | 1.56 |
| *Escherichia coli* K-12 ML 1630 | >100 | 12.5 | 12.5 | 0.78 | 1.56 |
| *Escherichia coli* K-12 ML 1410 | 6.25 | 12.5 | 12.5 | 1.56 | 1.56 |
| *Escherichia coli* K-12 ML 1410 R81 | >100 | 50 | 50 | 1.56 | 1.56 |
| *Escherichia coli* LA 290 R55 | >100 | >100 | >100 | 50 | 25 |
| *Escherichia coli* LA 290 R56 | 25 | 100 | 100 | 12.5 | 3.13 |
| *Escherichia coli* LA 290 R64 | 25 | 50 | 100 | 6.25 | 3.13 |
| *Escherichia coli* W 677 | 3.13 | 6.25 | 6.25 | 0.20 | 0.39 |
| *Escherichia coli* JR 66/W677 | >100 | >100 | >100 | 50 | 50 |
| *Klebsiella pneumoniae* PCI 602 | 3.13 | 6.25 | 25 | 0.39 | 0.39 |
| *Klebsiella pneumoniae* 22 No. 3038 | >100 | >100 | >100 | 100 | 50 |
| *Pseudomonas aeruginosa* A3 | >100 | 12.5 | 100 | 1.56 | 1.56 |
| *Pseudomonas aeruginosa* No. 12 | 100 | 100 | 100 | 0.78 | 0.78 |
| *Pseudomonas aeruginosa* TI-13 | >100 | 50 | 100 | 1.56 | 0.78 |
| *Pseudomonas aeruginosa* GN 315 | >100 | 50 | 100 | >100 | 100 |
| 99 | >100 | 100 | >100 | 3.13 | 1.56 |
| *Pseudomonas aeruginosa* H 11 | >100 | 50 | 100 | — | — |

From the above Table, it is seen that the new compounds, 3'-deoxykanamycin C and 3',4'-dideoxykanamycin C according to the present invention inhibits the growth of many kinds of bacterial strains. These new compounds have a low toxicity to animals and men as shown by the fact that these compounds exhibits an $LD_{50}$ value of more than 300 mg/kg upon intravenous injection in mice. Accordingly, the new compounds of the present invention are useful for chemotherapeutic treatment of infections caused by gram-negative and gram-positive bacteria.

3'-Deoxykanamycin C and 3',4'-dideoxykanamycin C which are the new compounds of the present invention are not inactivated by aminoglycoside 3'-phosphotransferases and 6'-acetyltransferases. The 6'-acetyltransferases which acetylate the 6'-amino group of kanamycins A and B, 3'-deoxykanamycin B and 3',4'-dideoxykanamycin B, are widely distributed in clinically isolated resistant bacteria. Actually, 3'-deoxykanamycin C is more active than kanamycin B derivatives against resistant strains which produce 6'-acetyltransferases, for example *Pseudomonas aeruginosa* GN315. Moreover, owing to the lack of the 3'-hydroxyl group, the deoxy-kanamycin C compounds of the present invention are effective against resistant bacteria which produce 3'-phosphotransferases. Therefore, 3'-deoxykanamycin C and 3',4'-dideoxykanamycin C will prevent infections of various kinds of resistant bacteria, and may be used as the synthetic intermediate for synthesis of more useful drugs such as 1-N-acyl derivatives with L-4-amino-2-hydroxybutyric acid.

Furthermore, the new compounds of the present invention are of a remarkably low toxicity to animals, including men, as described above. This is in contrast to the fact that the known 3'-deoxykanamycin B and 3',4'-dideoxykanamycin B have a higher toxicity to animals, as these substances show $LD_{50}$ values of 159 mg/kg and 109 mg/kg, respectively, upon intravenous injection in mice. 3'-Deoxykanamycin C and 3',4'-dideoxykanamycin C are inferior in their antibacterial activity against some bacteria strains to 3'-deoxykanamycin B and 3',4'-dideoxykanamycin B, but this inferiority is compensated for by the remarkably lower toxicity of 3'-deoxykanamycin C and 3',4'-dideoxykanamycin C than that of the deoxyderivatives of kanamycin B, because the deoxykanamycin C compounds of the present invention are safe to be administered in a dosage of 2 to 3-fold much than the usual dosage of the deoxy derivatives of kanamycin B.

The new deoxy-kanamycin C compounds of the present invention may readily be converted into a form of a pharmaceutically acceptable acid-addition salt such as the hydrochloride, sulfate, phosphate, nitrate, acetate, maleate, fumarate, succinate, tartarate, oxalate, citrate, ascorbate, methanesulfonate, ethanesulfonate and the like by reacting the free base form of 3'-deoxykanamycin C or 3',4'-dideoxykanamycin C with the appropriate acid in aqueous medium. The new deoxy-kanamycin C compounds of the present invention and their pharmaceutically acceptable acid-addition salt may be administered orally, intraperitoneally, intravenously, subcutaneously or intramuscularly using any pharmaceutical form known to the art for such administration and in a similar manner to the known kanamycins. For instance, the new compounds of the formula (I') of the present invention may be administered orally using any pharmaceutical form known to the art for oral administration. Examples of the pharmaceutical forms for oral administration are powders, capsules, tablets, syrup and the like. A suitable dose of the new compounds of the present invention for effective treatment of bacterial infections is in a range of 0.25 to 2 g. per person a day when it given orally. It is preferred that said dose should be orally administered in 3 to 4 aliquots per day. The new compounds of the present invention may also be administered by intramuscular injection at a dosage of 100 to 1000 mg per person two to four times per day. Moreover, the new compounds of the present invention may be formulated into an ointment for external application which contains a compound of the present invention at a concentration of 0.5–5% by weight in mixture with a known ointment base such as polyethylene glycol. Furthermore, the new compounds of the present invention is useful for use in sterilization of surgical instruments.

According to a third aspect of the present invention, therefore, there is provided an antibacterial composition comprising as the active ingredient 3'-deoxykanamycin C, 3',4'-dideoxykanamycin C or its acid-addition salt in an antibacterially effective amount to inhibit the growth of bacteria, incombination with a carrier for the active ingerdient.

The present invention is now illustrated with reference to the following Examples but to which the present invention is limited.

EXAMPLE 1

Synthesis of Kanamycin C (a) Preparation of 6'-N-t-butoxycarbonylkanamycin B

A solution of 9.66 g. (20 milimole) of kanamycin B in 200 ml. of water was admixed with a solution of 4.80 g. (20 milimole) of t-butyl S-4,6-dimethylpyrimid-2-ylthiocarbonate, (a reagent for introduction of an amino-protecting group) in 200 ml. of dioxane, and the admixture so obtained was stirred for 18 hours at ambient temperature. The reaction mixture was concentrated to dryness under reduced pressure. The solid residue was taken up into water and the resulting aqueous solution was passed through a column of 700 ml. of a cation-exchange resin, Amberlite CG 50 (ammonium form) for adsorption of the formed 6'-N-t-butoxycarbonylkanamycin B. The resin column was washed with 2800 ml. of water and then eluted with 0.2% aqueous ammonia. The eluate was collected in 20 ml.fractions, and such fractions which gave a reaction positive to ninhydrin and gave a single spot (positive to ninhydrin) in a high-voltage filter paper electrophoresis were combined together and concentrated to dryness under reduced pressure, affording 4.70 g. of a white colored powder comprising 6'-N-BOC-kanamycin B. Yield 40%. The resin column was further eluted with 0.6% aqueous ammonia to recover 2.0 g. of unreacted kanamycin B. Recovery yield 21%.

(b) Preparation of penta-N-protected derivative(IV)

6'-N-t-butoxycarbonylkanamycin B (3 g., 5.15 milimole) obtained in the preceding step (a) was dissolved in 75 ml. of methanol, and the resulting methonolic solution was admixed with 37.5 ml. of acetic anhydride. The mixture was stirred at ambient temperature for 5 hours to effect the acetylation of the remaining amino groups. The reaction solution was concentrated to dryness under reduced pressure, and the solid residue was washed with about 50 ml. of ethyl ether to give 4.04 g. of a powder of 6'-N-t-butoxycarbonyltetra-N-acetylkanamycin B.

(c) Preparation of the 6'-amino derivative (V)

The powdery penta-N-protected derivative (IV) (3.93 g.) obtained in the preceding step (b) of this Example was dissolved in 35 ml. of an aqueous solution of 90% trifluoroacetic acid, and the resulting mixture was allowed to stand for 45 minutes at ambient temperature to effect the removal of the BOC group from the 6'-position. The reaction mixture was concentrated to dryness under reduced pressure, and the solid residue was washed with about 50 ml. of ethyl ether to give 4.03 g. of a white colored powder of the tetra-N-acetyl derivative, that is, 1,3,2',3''-tetra-N-acetylkanamycin B.

(d) Preparation of the 6'-hydroxyl derivative (VI) and removal of the protective groups The powdery 6'-amino derivative (V) obtained in the preceding step (c) of this Example was dissolved in 66 ml. of an aqueous solution of 33% acetic acid, and to the resulting solution were added a solution of 5.4 g. of sodium nitrite in 66 ml. of water and then 33 ml. of acetic acid under ice-cooling and stirring. The admixture was stirred for 1 hour under ice-cooling and then for 2 hours at ambient temperature to effect the reaction where the 6'-amino group was converted into the 6'-hydroxyl group. The reaction solution was concentrated to dryness under reduced pressure to leave 10.05 g. of the solid residue. This solid comprising the formed 1,3,2',3''-tetra-N-acetylkanamycin C was taken up into 80 ml. of 2N aqueous sodium hydroxide, and the resulting mixture was heated for 12.5 hours under reflux to effect the removal of the acetyl groups.

After admixing with 5 l. of water, the reaction solution was passed through a column (inner diameter 3.6 cm.) of 1 l. of a cation-exchange resin, Amberlite CG-50 (70% ammonium form) for the adsorption of the kanamycin C derivative. The resin column was washed with 6 l. of water and then eluted with 0.5N aqueous ammonia. The eluate was collected in 19 ml.-fractions, and fractions Nos. 103 to 118 as combined together were concentrated to dryness under reduced pressure to afford 1.98 g. of a crude powder of kanamycin C. This crude powder was taken up into 50 ml. of water and again passed through a column (inner diameter 2 cm.) of 200 ml. of Amberlite CG-50 ($NH_4$ form). The resin column was washed with 600 ml. of water and then eluted successively with 600 ml. of 0.05N aqueous ammonia, with 600 ml. of 0.1N aqueous ammonia and with 900 ml. of 0.2N aqueous ammonia. The eluate was collected in 15 ml.-fractions, and the fraction Nos. 67 to 92 were combined together and concentrated to dryness under reduced pressure, affording 1.14 g. (2.37 milimole) of a colorless purified powder of kanamycin C. Yield 47%. This product was confirmed to be identical with an authetic sample of kanamycin C obtained by the fermentative method using *Streptomyces kanamyceticus.*

EXAMPLE 2

Synthesis of 3'-deoxykanamycin C

(a) Preparation of 6'-N-t-butoxycarbonyl-3'-deoxykanamycin B

A solution of 2.0 g. (4.3 milimole) of 3'-deoxykanamycin B in 40 ml. of water was admixed with a solution of 1.03 g. (4.7 milimole) of t-butyl S-4,6-dimethylpyrimid-2-ylthiocarbonate in 40 ml. of dioxane, and the admixture so obtained was stirred for 24 hours at ambient temperature. The reaction mixture was then concentrated to dryness under reduced pressure, and the solid residue was taken up into 32 ml. of water. The resultant aqueous solution was passed through a column of 160 ml. of a cation-exchange resin, Amberlite CG-50 (ammonium form) for adsorption of the formed 6'-N-t-butoxycarbonyl-3'-deoxykanamycin B. The resin column was washed with 800 ml. of water and then eluted with 800 ml. of 0.1N aqueous ammonia. The eluate was collected in 15 ml.-fractions, and the fraction Nos. 26 to 42 were combined together and concentrated to dryness under reduced pressure to give 1.06 g. of a white colored powder comprising 6'-N-t-butoxycarbonyl-3'-deoxykanamycin B. Yield 44%. The resin column was further eluted with 0.5N aqueous ammonia to recover 452 mg. of unreacted 3'-deoxykanamycin B. Recovery efficiency 23%.

(b) Preparation of penta-N-protected derivative (IV)

A solution of 211 mg. (0.37 milimole) of 6'-N-t-butoxycarbonyl-3'-deoxykanamycin B in 5 ml. of methanol was admixed with 2.5 ml. of acetic anhydride, and the admixture was agitated for 5 hours at ambient temperature for the acetylation of the remaining amino groups. The reaction solutuion was admixed with a volume of water and then concentrated to dryness under reduced pressure to give a powder comprising 6'-N-t-butoxycarbonyl-tetra-N-acetyl-3'-deoxykanamycin B. Yield 296 mg.

(c) Preparation of 6'-amino derivative (V)

The powdery penta-N-protected derivative (IV) (235 mg.) obtained in the preceding step (b) of this Example was dissolved in 2 ml. of an aqueous solution of 90% trifluoroacetic acid and the resulting mixture was allowed to stand for 45 minutes at ambient temperature to effect the removal of the BOC group from the 6'-position of the penta-N-protected derivative (IV). The reaction mixture was concentrated to dryness under reduced pressure, and the solid residue obtained was washed with about 2 ml. of ethyl ether to give 227 mg. of a white colored powder comprising the tetra-N-acetyl derivative, that is, 1,3,2',3''-tetra-N-acetyl-3'-deoxykanamycin B.

(d) Preparation of 6'-hydroxyl derivative (VI) and removal of the protective groups The powdery 6'-amino derivative (V) (193 mg.) obtained in the preceding step (c) of this Example was dissolved in 3.2 ml. of an aqueous solution of 33% acetic acid, and to the resulting solution was added a solution of 265 mg. of sodium nitrite in 3.2 ml. of water and then 1.6 ml. of acetic acid under ice-cooling and stirring. The mixture so obtained was stirred for 1 hour under ice-cooling and then for 16 hours at ambient temperature to effect the reaction where the 6'-amino group was converted into the 6'-hydroxyl group. The reaction solution was concentrated to dryness under reduced pressure to obtain 240 mg. of a solid residue. This solid comprosing 1,3,2',3''-tetra-N-acetyl-3'-deoxykanamycin C was taken up into 4 ml. of 2N aqueous sodium hydroxide, and the resulting mixture was heated for 7 hours under reflux to effect the removal of the acetyl groups.

The reaction solution so obtained was admixed with 200 ml. of water and then passed through a column (inner diameter 1.6 cm.) of 50 ml. of a cation-exchange resin, Amberlite CG-50 (70% ammonium form) for the adsorption of the formed kanamycin C derivative. The resin column was washed with 250 ml. of water and then eluted with 0.5N aqeous ammonia. The eluate was collected in 10 ml.-fractions, and the fraction Nos. 58 and 59 were combined together and concentrated to dryness under reduced pressure to give 89 mg. of a crude powder of 3'-deoxykanamycin C. This crude powder was taken up into 2 ml. of water, and the aqueous solution obtained was rechromatographed using a column (inner diameter 0.75 cm.) of 10 ml. of Amberlite CG-50 (ammonium form) in such a manner that after washing with 30 ml. of water, the resin column was eluted with 45 ml. of 0.1N aqeous ammonia, and then with 45 ml. of 0.2N aqeous ammonia. The eluate was collected in 1 ml.-fraction, and the fraction Nos. 78 to 91 as combined together were concentrated to dryness under reduced pressure. A colorless purified powder of 3'-deoxykanamycin C (54 mg.; 0.11 milimole) was afforded. Yield 45%.

EXAMPLE 3

Synthesis of 3',4'-dideoxykanamycin C (a) Preparation of 6'-N-benzyloxycarbonyl-3',4'-dideoxykanamycin B To a solution of 13.53 g. (30 milimole) of 3',4'-dideoxykanamycin B in 135 ml. of water was dropwise added over 1 hour 5.61 g. (33 milimole) of benzyloxycarbonyl chloride under ice-cooling and stirring. After the dropwise addition was completed, the admixture so obtained was stirred for 1 hour at ambient temperature and the precipitate as formed was removed by filtration. The filtrate was washed with 135 ml. of ethyl ether, and the aqueous layer was neutralized by addition of aqueous ammonia and then concentrated under reduced pressure. The concentrated solution so obtained was passed through a column of 480 ml. of a cation-exchange resin, Amberlite CG-50 (ammonium form) for adsorption of the formed 6'-N-benzyloxycarbonyl-3',4'-dideoxykanamycin B. The resin column was washed with 1920 ml. of water and then eluted with 0.1N aqueous ammonia. The first running (960 ml.) of the eluate was discarded and the subsequent running (780 ml.) was collected and concentrated to dryness under reduced pressure to give 5.43 g. of a white colored powder comprising 6'-N-benzyloxycarbonyl-3',4'-dideoxykanamycin B. Yield 31%. The column was further eluted with 0.5N aqueous ammonia to recover 2.7 g. of unreacted 3',4'-dideoxykanamycin B. Recovery efficiency 20%.

(b) Preparation of penta-N-protected derivative (IV)

6'-N-Benzyloxycarbonyl-3',4'-dideoxykanamycin B (1.59 g.; 2.72 milimole) was admixed with 160 ml. of acetic anhydride and 16 g. of sodium acetate, and the admixture so obtained was heated for 2 hours under reflux (at 110° C.) to effect the acetylation. The reaction mixture was concentrated to dryness under reduced pressure, and the solid residue was extracted with about 100 ml. of acetone. The extract in acetone was concentrated to dryness under reduced pressure, leaving a solid (2.5 g.). This solid was taken up into 10 ml. of chloroform, and the resulting solution was passed through a column (inner diameter 2.6 cm.) of 150 g. of silica gel for adsorption of the formed acetylation product. The silica gel column was washed with 350 ml. of chloroform and then eluted successively with 900 ml. of chloroform-methanol (30:1 by volume), with 900 ml. of chloroform-methanol (15:1 by volume) and with chloroform-methanol (10:1 by volume). The eluate was collected in about 14 ml.-fractions. The fraction Nos. 91 to 149 as combined together were concentrated to dryness under reduced pressure to give 1.80 g. of a white colored powder compriding 6'-N-benzyloxycarbonyl-tetra-N-acetyl-tetra-O-acetyl-3',4'-dideoxykanamycin B.

(c) Preparation of 6'-amino derivative (V)

The white colored powder (1.18 g.) obtained in the above step (b) of this Example was dissolved in a mixture of 20 ml. of methanol and 5 ml. of water, and the resulting solution was subjected to catalytic reduction for 45 minutes under a stream of hydrogen and in the presence of 1.61 g. of 5% palladium-on-barium carbonate added to said solution, so that the benzyloxycarbonyl group was removed. After removal of the catalyst by filtration, the reaction mixture was concentrated to dryness under reduced pressure, affording 942 mg. of a white colored powder of the 6'-amino derivative, that is, 1,3,2',3''-tetra-N-acetyl-5,2'',4'',6''-tetra-O-acetyl-3',4'-dideoxykanamycin B.

(d) Production of 6'-hydroxyl derivative (VI) and removal of the protective groups The white colored powder (942 mg.) of the 6'-amino derivative (V) obtained in the above step (c) of this Example was dissolved in 16 ml. of a solution of 33% acetic acid in water, and to the resulting solution were added 16 ml. of a solution of 1.24 g. of sodium nitrite and then 8 ml. of acetic acid under ice-cooling and stirring. The admixture so obtained was stirred for 1 hour under ice-cooling and then for 3 hours at ambient temperature to effect the conversion of the 6'-amino group into 6'-hydroxyl group. The reaction mixture was concentrated to dryness under reduced pressure, and the solid residue was dissolved in 3 ml. of chloroform. The solution in chloroform was passed through a column (inner diameter 2 cm.) of 100 g. of silica gel, which was then washed with 210 ml. of chloroform and thereafter eluted successively with 660 ml. of chloroform-methanol (50:1 by volume), with 1750 ml. of chloroform-methanol (30:1 by volume), with 900 ml. of chloroform-methanol (10:1 by volume) and with 700 ml. of chloroform-methanol (5:1 by volume). The eluate was collected in about 14 ml.-fractions. The fraction Nos. 220 to 270 as combined together were concentrated to dryness under reduced pressure, giving 587 mg. of a white colored powder of tetra-N-acetyl-tetra-O-acetyl-3',4'-dideoxykanamycin C.

This white colored powder (234 mg.) was taken up into 4 ml. of 2N aqueous sodium hydroxide, and the resulting solution was heated for 7 hours under reflux to effect the removal of the acetyl groups. The reaction solution was dissolved in 200 ml. of water and then passed through a column (inner diameter 1.6 cm.) of 50 ml. of a cation-exchange resin, Amberlite CG-50 (70% ammonium form) for adsorption of the desired product. After washing with 250 ml. of water, the resin column was eluted with 0.5N aqueous ammonia to yield 122 mg. of a crude powder of 3',4'-dideoxykanamycin C. A solution of this crude powder in 2 ml. of water was passed through a column (inner diameter 0.8 cm.) of 14 ml. of Amberlite CG-50 NH₄ form) for adsorption of the desired product. After washing with 45 ml. of water, the resin column was eluted with 40 ml. of 0.05N aqueous ammonia, then with 70 ml. of 0.1N aqueous ammonia and finally with 70 ml. of 0.2N aqueous ammonia. The eluate was collected in 1 ml.-fractions, and the fractions Nos. 119 to 146 were combined together and concentrated to dryness under reduced pressure to give 90 mg. of a colorless purified powder of 3′,4′-dideoxykanamycin C. Overall yield 23%.

What we claim is:

1. A process for the production of a kanamycin C compound of the formula (I):

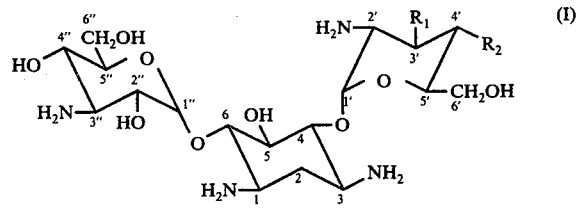

wherein $R_1$ and $R_2$ each is hydroxyl, or $R_1$ is hydrogen and $R_2$ is hydroxyl, or $R_1$ and $R_2$ each is hydrogen, which comprises the steps of:

protecting with t-butoxycarbonyl or benzyloxycarbonyl as an amino-protecting group the primary 6′-amino group of a kanamycin B compound represented by the general formula (II):

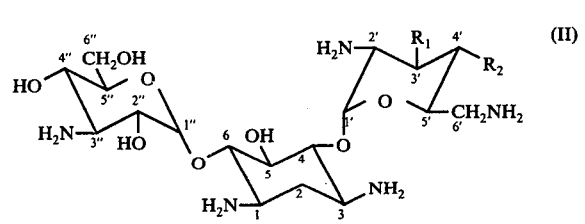

wherein $R_1$ and $R_2$ have the same meanings as defined above, to produce the 6′-N-protected derivative of said kanamycin B compound, protecting with acetyl as another amino-protecting group the remaining four, secondary amino groups of the 6′-N-protected derivative of the kanamycin B compound, to produce the penta-N-protected derivative of said kanamycin B compound, removing selectively by catalytic reduction with hydrogen or by trifluoroacetic acid the amino-protecting group from the primary 6′-amino group of the penta-N-protected derivative, to prepare the 1,3,2′,3″-tetra-N-protected derivative of said kanamycin B compound, treating the primary 6′-amino group so liberated of the 1,3,2′,3″-tetra-N-protected derivative with an alkali metal nitrite to convert the 6′-amino group into a hydroxyl group and thereby to produce the corresponding 6′-hydroxyl derivative, and removing by alkaline hydrolysis the amino-protecting group from the four secondary amino groups of the 6′-hydroxyl derivative, to produce the compound of the formula (I).

2. A process according to claim 1, in which the treatment of the 1,3,2′,3″-tetra-N-protected derivative with an alkali metal nitrite is carried out by admixing a solution of the 1,3,2′,3″-tetra-N-protected derivative in aqueous acetic acid with aqueous sodium nitrite under ice-cooling and stirring, and then allowing the admixture to raise to ambient temperature and to effect the conversion of the 6′-amino group.

3. A deoxykanamycin C compound of the formula (I′):

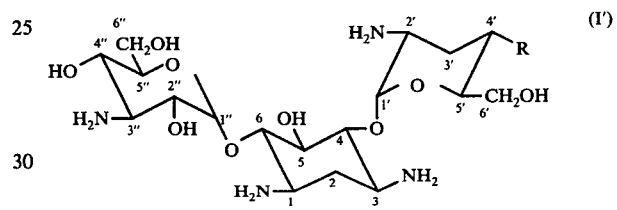

wherein R is a hydroxyl group or hydrogen atom, or a pharmaceutically acceptable acid-addition salt thereof.

4. 3′-deoxykanamycin C or a pharmaceutically acceptable acid-addition salt thereof.

5. 3′,4′-dideoxykanamycin C or a pharmaceutically acceptable acid-addition salt thereof.

6. An antibacterial composition comprising as the active ingredient deoxykanamycin C compound according to claim 3, in an antibacterially effective amount to inhibit the growth of bacteria, in combination with a carrier for the active ingredient.

* * * * *